US005580460A

United States Patent [19]

Polaschegg

[11] Patent Number: 5,580,460

[45] Date of Patent: Dec. 3, 1996

[54] PROCESS FOR DETERMINING THE OPERABILITY OF THE STRUCTURAL COMPONENTS IN THE DIALYSIS SECTION OF A DIALYZER OF A HEMODIALYSIS APPARATUS AND APPARATUS FOR EXECUTING THIS PROCESS

[75] Inventor: Hans-Dietrich Polaschegg, Oberursel, Germany

[73] Assignee: Fresenius AG, Germany

[21] Appl. No.: 501,162

[22] Filed: Jul. 11, 1995

Related U.S. Application Data

[63] Continuation of Ser. No. 156,784, Nov. 24, 1993, abandoned.

[30] Foreign Application Priority Data

Nov. 27, 1992 [DE] Germany .......................... 42 39 937.8

[51] Int. Cl.[6] ............................ B01D 61/30; B01D 61/32

[52] U.S. Cl. ............................ 210/646; 210/90; 210/138; 210/433.1; 210/741; 604/5

[58] Field of Search ........................ 210/90, 143, 321.71, 210/433.1, 434, 646, 741, 790, 929, 138; 604/4–6

[56] References Cited

U.S. PATENT DOCUMENTS

| | | | |
|---|---|---|---|
| 3,946,731 | 3/1976 | Lichtenstein | 210/929 |
| 3,976,574 | 8/1976 | White | 210/929 |
| 3,990,973 | 11/1976 | Boag et al. | 210/929 |
| 4,370,983 | 2/1983 | Lichtenstein | 210/929 |
| 4,517,081 | 5/1985 | Amiot et al. . | |
| 4,680,122 | 7/1987 | Barone | 210/646 |
| 4,834,888 | 5/1989 | Polaschegg | 210/646 |
| 4,894,164 | 1/1990 | Polaschegg | 210/646 |
| 4,997,570 | 3/1991 | Polaschegg | 210/646 |
| 5,092,836 | 3/1992 | Polaschegg | 210/646 |
| 5,247,434 | 9/1993 | Peterson et al. | 210/646 |

FOREIGN PATENT DOCUMENTS

| | | | |
|---|---|---|---|
| 0407737A1 | 1/1991 | European Pat. Off. . | |
| 3444671A1 | 6/1986 | Germany | 210/646 |
| 3600227A1 | 7/1987 | Germany | 210/646 |
| 3938662A1 | 7/1991 | Germany | 210/646 |

*Primary Examiner*—Joseph W. Drodge
*Attorney, Agent, or Firm*—Sterne, Kessler, Goldstein & Fox P.L.L.C.

[57] ABSTRACT

A method and apparatus for monitoring the operability of components in a hemodialysis apparatus during dialysis treatment. The dialyzer is isolated from the dialyzing liquid circuit for a time interval during dialysis treatment. During the isolation time interval, the dialyzing liquid circuit pressure is measured and monitored to detect deviations from a mean dialyzate operating pressure. The isolation is repeated periodically, with the time period between isolation intervals dependent upon the ultrafiltration coefficient of the dialyzer. This method may be performed automatically by a microprocessor in the hemodialysis apparatus.

21 Claims, 5 Drawing Sheets

A
B
C
D
I
II
1
1a
1b
2
2a
3
3a
4
5
6
6a
7
8
9
10
11
12
12a
13
14
15
16
17a
17b
17c
18
19
20
21
21a
22

23
ΔUF
UFK
Δt
A
p
22

24
Ta1
p (22)
Ta2
A
26
25 p [mmHg]
180.
140.
100.
60.0
20.0
200.
600.
1000
1400
1800
t in 1/100 sec
A
B
$t_0$
T
delta T
delta p p [mmHg]
180.
140.
100.
60.0
20.0
200.
600.
1000
1400
1800
t in 1/100 sec
delta T
delta p
T
$t_0$

PROCESS FOR DETERMINING THE OPERABILITY OF THE STRUCTURAL COMPONENTS IN THE DIALYSIS SECTION OF A DIALYZER OF A HEMODIALYSIS APPARATUS AND APPARATUS FOR EXECUTING THIS PROCESS

This application is a continuation of application Ser. No. 08/156,784, filed Nov. 24, 1993, now abandoned.

BACKGROUND OF THE INVENTION

Process for determining the operability of the structural components of the dialyzate section of a dialyzer of a hemodialysis apparatus, comprising volumetrical ultrafiltration in the dialysis liquid circuit and a control system for the ultrafiltration rate connected to a pressure transducer on the outlet of the dialyzer downstream of the associated dialyzer valve and a safety system based on monitoring of the transmembrane pressure, whereby the march of pressure (pressure as a function of time) in the dialyzer in the dialyzer liquid circuit is drawn upon when the dialyzer is in switched off state by detection of the signals of the pressure transducer to determine operability, together with the corresponding apparatus for executing this process.

Hemodialysis apparatus with volumetrical ultrafiltration (UF) control have found broad application. Appliances of this type are produced and marketed, e.g. by the applicant (hemodialysis apparatus of the Fresenius Company Series 2008 C, D, E). The UF control arrangement of these appliances permits predetermination of a specified ultrafiltration rate resp. ultrafiltration quantity. It then ensures that the predetermined ultrafiltration rate resp. quantity is withdrawn during the heamodialysis treatment, independently of the viscosity of the blood to be treated and the properties of the hemodialyzer.

It is known that such a control arrangement may lose its capacity for precise control of the ultrafiltration rate as a result of a defect.

Since, for example, a dramatic increase in the ultrafiltration rate caused by such a defect may endanger the patient, established safety standards (IEC 601 Section 16) require that a safety system must be present, which prevents an ultrafiltration dangerous to the patient. Monitoring of the transmembrane pressure (TMP) is accepted as such a safety system.

The development of dialyzers with membranes of high permeability—so-called high-flux dialyzers—has, however, resulted in the fact that, due to the limited resolution of the TMP sensor, TMP monitoring cannot determine a dangerously high or low ultrafiltration rate with sufficient resolution.

To ensure that at least the treatment starts with an intact ultrafiltration control system, arrangements have come into the market which permit manual or automatic examination of the integrity of the control system prior to treatment. This examination occurs by means of a pressure maintaining or holding test in the dialyzate section of the apparatus.

Experience has shown that technical apparatus usually becomes defective during operation and not in disconnected state.

The invention therefore proceeds from the problem of providing a process which also facilitates determination of the operability of the control system for the ultrafiltration rate during dialysis treatment by means of a pressure maintaining test, without additional devices for pressure variation.

This problem is solved, proceeding from the process specified above, in that during dialysis the dialyzer is periodically separated from the dialyzer is liquid circuit for a brief time interval respectively, during which the average dialyzate operating pressure is stable in tight state, and the march of pressure in the dialyzing liquid circuit of the separated dialyzer is monitored in the manner of a pressure maintaining test known per se for deviation from the stable state.

The process detects defective ultrafiltrations which may become dangerous in the current operating state by simple means.

To create realistic conditions, the process is usefully executed in such manner that the time interval during which the pressure maintaining test is performed typically is in the range of 20 seconds.

Since the threshold for defective ultrafiltration is reached differently in the case of error, depending on the ultrafiltration coefficient of the dialyzer used, the process is executed according to a further development of the invention in such manner that the period between two pressure maintaining test intervals is determined on the basis of the ultrafiltration coefficient of the dialyzer used in accordance with the equation $$\Delta t = (\Delta UF/p^{*}\ (60/UFC))$$

whereby Δt=period, ΔUF=max. error of the ultrafiltration, p=transmembrane pressure and UFC=ultrafiltration coefficient (volume per unit of time and unit of pressure).

The process may be executed manually or automatically. An apparatus for automatic execution of the process is usefully characterized according to the invention in that a microprocessor system which periodically generates switching signals in predetermined intervals for separating the dialyzer from the dialyzing liquid circuit for a predetermined time interval is provided in the hemodialysis apparatus, whereby, in addition to the signal of the pressure transducer, all necessary values are fed to the microprocessor and the microprocessor generates an indicator/alarm/switch signal depending on the march of pressure during the time interval.

Further developed features of the invention as well as features concerning the determination of the operability of an arrangement of the hemodialysis apparatus connected to the ultrafiltration control arrangement are shown in the description passages relating to the exemplary embodiments shown in the drawing.

BRIEF DESCRIPTION OF THE FIGURES

The Figures show:

FIG. 1 shows in schematic presentation (including a flow diagram) a known hemodialysis apparatus, the apparatus A 2008C of the Fresenius company. The dialyzer 1 with the extracorporeal circuit I and the dialyzing liquid circuit II whose tube systems are also only presented schematically, is the central component of this apparatus.

Figure 1:
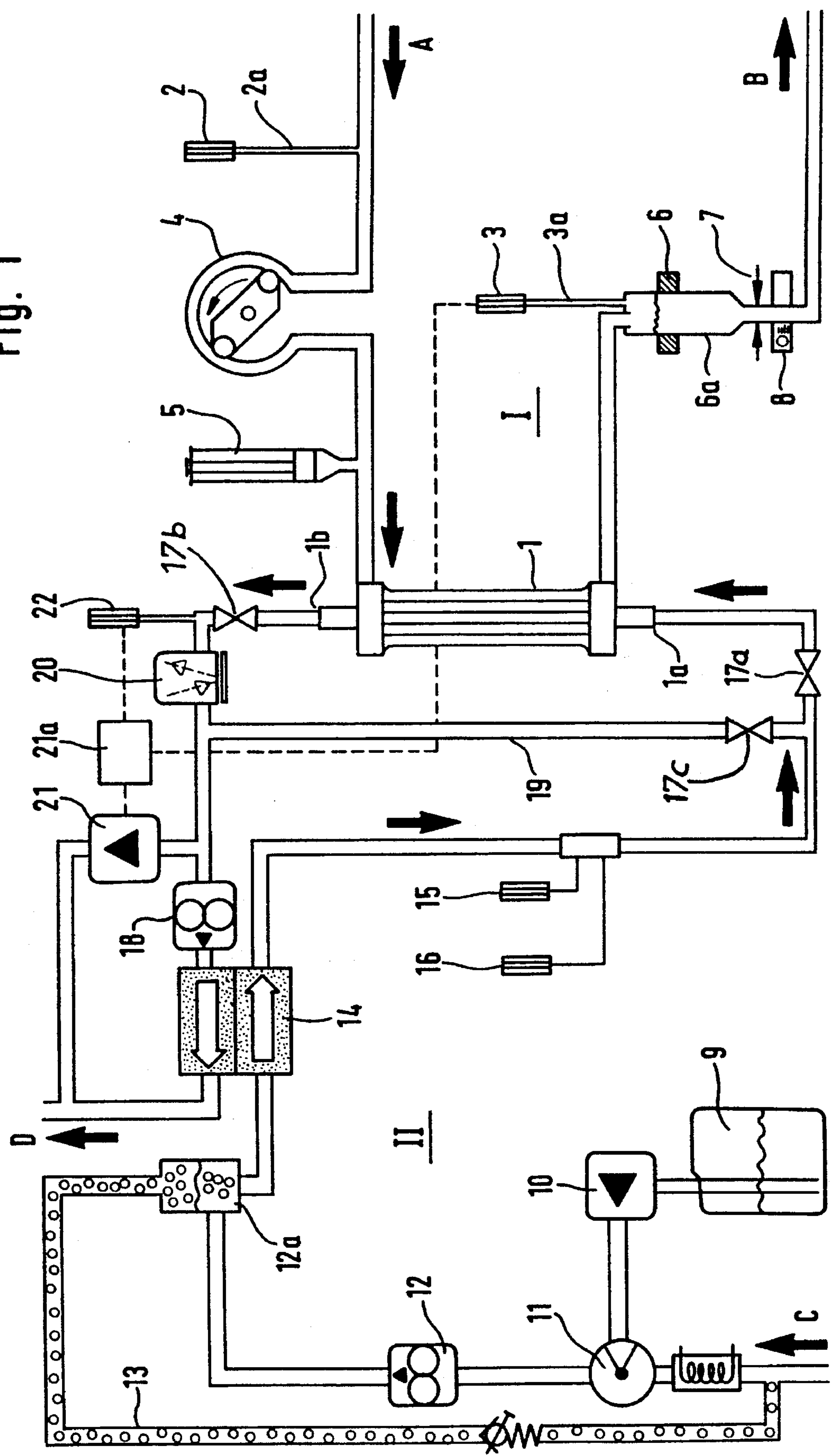
FIG. 1—the block diagram of a known hemodialysis appliance, wherein the process and apparatus according to the invention are preferably used.

Dialyzers are commercially available in many variants. A hemoflow capillary dialyzer is preferably used.

In the circuit section leading from the patient to the dialyzer 1, the blood tube system (direction arrow A), arterial pressure measurement first takes place. The arterial pressure measurement occurs by means of a piezo-resistive pressure transducer 2, to which the pressure measuring duct 2*a* of the blood tube system is connected, whereby a hydrophobic membrane filter (not shown) is interposed as a contamination preventor.

In the same manner, measurement of the venous reflux pressure is effected in the circuit section leading to the patient (direction arrow B), by means of a pressure transducer 3 via pressure measuring duct 3*a*.

A blood pump 4, in particular in the form of the well known peristaltic tube pump, effects the blood flow in the extracorporeal circuit I.

A heparin pump 5 provides for continuous feed of the necessary heparin dose to prevent blood coagulation.

Downstream of the dialyzer 1 an air detector 6 is further provided, which prevents infusion of blood foam or air, which has entered the extracorporeal circuit I, into the patient. It comprises a drip chamber support accommodating the venous drip chamber 6*a* of the blood tube system. The air detector 6 recognizes whether air bubbles or microfoam are present in the drip chamber 6*a* by means of ultrasound impulses.

In case of danger, an electromagnetic tube throttle clamp 7 closes the venous reflux to the patient by stopping blood pump 4.

An additional optical system 8 in the tube support under drip chamber 6*a* recognizes whether blood is present in the tube or whether normal saline solution (or possibly also air) is present.

In the dialyzing liquid circuit II the dialyzing liquid for the dialysis is produced from water (arrow C) and concentrate in the ratio 34:1, degassed and heated to body temperature.

For this purpose, concentrate is extracted from a concentrate container 9 by means of a pump 10 and fed to the mixing point 11, where mixing with water is effected. The degassing occurs by means of a geared pump 12, which generates a partial vacuum. The gas which bubbles into the air separator chamber 12*a* is fed back via duct 13.

The dialyzing liquid then flows through the lower part of a balancing chamber 14, in which the fresh dialyzing liquid flowing to dialyzer 1 is replaced by exactly the same amount of used liquid from the dialyzer. In addition to balancing, the balancing chamber also serves as a part of the mixing system. After each filling of a balancing chamber, a membrane pump pumps the correct amount of concentrate to the mixing point. A temperature sensor 15 and a conductivity sensor 16 are provided in the feed line to the dialyzer 1 to monitor the condition of the dialyzing liquid. In addition, a valve, the first dialyzer valve 17*a*, is located in the feed line. A further valve, the second dialyzer valve 17*b*, is provided in the outlet of dialyzer 1. A line, the bypass line 19, branches off in front of the first dialyzer valve 17*a* and discharges into the dialyzate system downstream from the second dialyzer valve 17*b*. Bypass valve 17*c* is interposed in this line 19. The valve 17*c* on the one hand and valves 17*a* and 17*b* on the other are actuated alternately. If valves 17*a* and 17*b* are closed and valve 17*c* is opened, dialyzer 1 is switched off and bridged by bypass line 19. If valves 17*a* and 17*b* are opened and valve 17*c* is closed, then the dialyzing liquid flows through the dialyzer.

The flow of the dialyzing liquid in circuit II is effected by a pump 18, the dialyzing liquid pump, which is arranged in the discharging line of the dialyzing liquid circuit II. The used liquid then flows through the upper part of balancing chamber 14 and subsequently reaches the drain (arrow D).

A turbidity of the dialyzing liquid flowing off is recognized by the blood leak control 20 with the aid of an infrared transmission process and indicated as a blood alarm. This process detects membrane ruptures or small blood leaks in the dialyzer.

A pump 21 connected to the discharge line, preferably a volumetrical membrane pump, withdraws liquid from the system at a predetermined rate. As a result, a negative pressure of between 0 and −540 mmHg, the transmembrane pressure, is generated, depending on the dialyzer; the liquid withdrawn by the membrane pump follows as ultrafiltrate (UF) from the blood and also reaches the drain (arrow D) or a separate collecting vessel.

The dialyzing liquid negative pressure is measured by an electronic pressure transducer 22 and, subtracted from the venous reflux pressure at sensor 3, is recorded as the transmembrane pressure (UF).

The medium transmembrane pressure (TMP) is defined as:

$$TMP = \frac{(P_{bi} + P_{bo})}{2} - \frac{(P_{di} + P_{do})}{2}$$

whereby $P_{hi}$=blood pressure on the inlet side of the dialyzer $P_{ho}$=blood pressure on the outlet side of the dialyzer $P_{di}$=dialyzing liquid pressure on the inlet side 1*a* of the dialyzer $P_{do}$=dialyzing liquid pressure on the outlet side 1*b* of the dialyzer.

All components of the extracorporeal blood circuit I are connected with each other by safety devices. A decrease of the blood level in the drip chamber 6*a* causes the air detector 6 to switch off the blood pump 4 and close the tube throttle clamp 7. The same applies to all blood alarms which may occur (blood leak alarm actuated by sensor 20, an increase or decrease of the arterial or venous or UF pressure above or below alarm limits signalled by sensors 2, 3 and 20). In addition displays (not shown) for the individual measuring signals are provided.

The balancing chamber 14 ensures that the same quantity of dialyzing liquid is always fed to resp. extracted from dialyzer 1.

In the concrete arrangement of the balancing chamber both chamber sections are separated by a membrane. Both chamber sections thereby have the same volume.

The operation of the balancing chamber is clockwise. During working cycle 1 the lower side of the balancing chamber fills with fresh dialyzing liquid. The pressure acts upon the membrane, and used dialyzing liquid flows into the drain.

During maximal expansion of the membrane the expelled liquid volume VA corresponds to the chamber volume.

In working cycle 2 the upper side of the balancing chamber fills with used dialyzing liquid. The fresh dialyzing liquid is pressed to the dialyzer. During maximal expansion of the membrane the expelled liquid volume VF corresponds to the chamber volume.

In both cases the volume of the liquid expelled from the one or the other chamber section is equal to the total volume of the chamber:

VF=chamber volume=VA

VF=VA

The use of only a single balancing chamber 14 would result in discontinuous dialyzing liquid flow. To achieve continuous flow of the dialyzing liquid, a further balancing chamber (not shown) is switched in parallel with the first chamber and operated in opposite sequence.

Further details of this balancing system can be drawn from the DE-A-28 38 414, to which reference is made.

Due to the discussed property of the balancing arrangement 14, no volume shift between the blood and the dialyzate side in the dialyzer 1 can occur either in the one or the other direction.

The so-called ultrafiltration rate would therefore be zero.

The section of the liquid circuit enclosed between balancing arrangement 14 and the dialyzer 1 behaves like a closed constant volume system. Pump 21 is provided to withdraw liquid from this system. Due to the above-mentioned properties of the balancing arrangement, the quantity of liquid withdrawn from the system by means of this pump must be replaced by an equally large quantity of liquid which passes from the blood side I to the dialyzate side II of the dialyzer 1. The quantity of liquid withdrawn by means of pump 21 thus corresponds to the quantity of liquid passing through the membrane of dialyzer 1, i.e. the ultrafiltrate.

A control device 21*a*, by means of which a monitored volume-controlled ultrafiltration can be achieved is associated with pump 21. This ultrafiltration (UF) control device 21*a* permits predetermination of a specific ultrafiltration rate or quantity.

The volume control therefore facilitates precise ultrafiltration in all dialyzer types. Thus the amount of liquid withdrawn during dialysis no longer depends on the blood pressure, the properties of the dialyzer or the manually adjusted negative pressure.

The control device 21*a*, however, can lose its capacity for precise control of the UF rate as a result of a defect. Both a considerably raised and a considerably lowered UF rate may, however, be dangerous to the patient. The control device 21*a* therefore comprises a safety system which prevents a UF rate dangerous to the patient. This safety system is based on monitoring of the transmembrane pressure TMP, as indicated schematically in FIG. 1 by the lines of action from the control/safety system 21*a* to sensors 22 and 3. This transmembrane pressure typically changes in the case of an error, e.g. a leak in the UF control system.

The development of dialyzers with membranes of high permeability, so-called high-flux dialyzers, has, however, resulted in the fact that TMP control cannot detect a dangerously high UF rate with sufficient resolution. This is demonstrated by the following calculation:

A high-flux dialyzer has an ultrafiltration coefficient (UFC) of 20–60 l/h mmHg (volume per unit of time and unit of pressure). A conventional TMP sensor has a resolution of 20 mmHg. A deviation from the nominal value of the TMP of 20 mmHg does therefore not yet lead to an alarm, although with a UFC of 20 it amounts to an excess ultrafiltration of 1 l/h and with a UFC of 60 one of 3 l/h. Deviations of more than 0.5 l can, however, already cause an unpleasant resp. dangerous blood pressure drop in the patient. A reverse ultrafiltration of this order is also equally dangerous, since it results in excessive hydration of the patient.

To at least ensure that the treatment begins with an intact or tight ultrafiltration control system, arrangements are known which permit manual or automatic examination of the integrity of the ultrafiltration control system. This occurs by means of a so-called pressure holding or maintaining test. The described UF control system is a closed system. In this system a negative resp. overpressure is generated by an additional pump and, after switching off the pump, the march of pressure is monitored with the assistance of the signals of the pressure transducer 22. If there is no or only minimal change in the pressure, the system is leakproof (tight) and therefore intact. If it is impossible to build up pressure or the pressure changes quickly, this signals a leak in the system. The system is therefore defective and the hemodialysis apparatus may not be used for treatment.

Experience has shown that technical apparatus normally becomes defective during operation and not in disconnected state. The described pressure holding test performed prior to treatment ensures that patients are not repeatedly treated with a defective apparatus, but it does not prevent a dangerous ultrafiltration caused by a defect during treatment.

To detect a defect during treatment before it causes dangerous effects, a pressure holding test may also be performed periodically by brief interruption of the dialysis. For this purpose, the dialyzer 1 is isolated by means of the dialyzer valves (17*a, b*) disposed upstream and downstream of the dialyzer. The bypass valve 17*c* is simultaneously opened. Then a pressure holding test is performed as described above. After the test is successfully concluded, the bypass valve is closed, the dialyzer valves are opened and the treatment is continued.

To generally create a negative pressure in the dialyzing liquid circuit, the ultrafiltration pump 21 already provided in the system is usually used. To generate positive pressure an additional pump is required. This may, for example, be provided by an air pump attached to the secondary air separator 12*a* operated in reverse, i.e. so as to pump air into the air separator.

Testing with positive and negative pressures is initially necessary in the above-specified pressure holding test, since at this point in time it is not known at which value the dialyzing liquid pressure shall come into effect, since there are leaks which are only effective in one pressure range.

The described pressure holding test would therefore require an additional pump compared to the apparatus according to FIG. 1, would be time-consuming and would result in an ultrafiltration error. In addition, it could detect a leak which is not acutely dangerous, since it is not effective at the current operating pressure. The dialysis treatment would then be interrupted unnecessarily.

SUMMARY OF THE INVENTION

The invention provides a process which requires no additional auxiliary means to generate positive resp. negative pressure deviations. The pressure holding test is hereby performed periodically during the dialysis at operating pressure. For this purpose the dialyzer 1 is separated from the dialyzing liquid circuit as described hereinabove, the bypass valve 17*c* is opened and the march of the operating pressure (pressure as a function of time) is observed by means of the march of the signal of the pressure transducer 22. This process is not only simpler, but it also only recognizes ultrafiltration errors which may become dangerous in the current operating condition. By means of relatively short-term observation of the march of pressure, leaks with app. 0.125 l/h can easily be detected.

Figure 5:
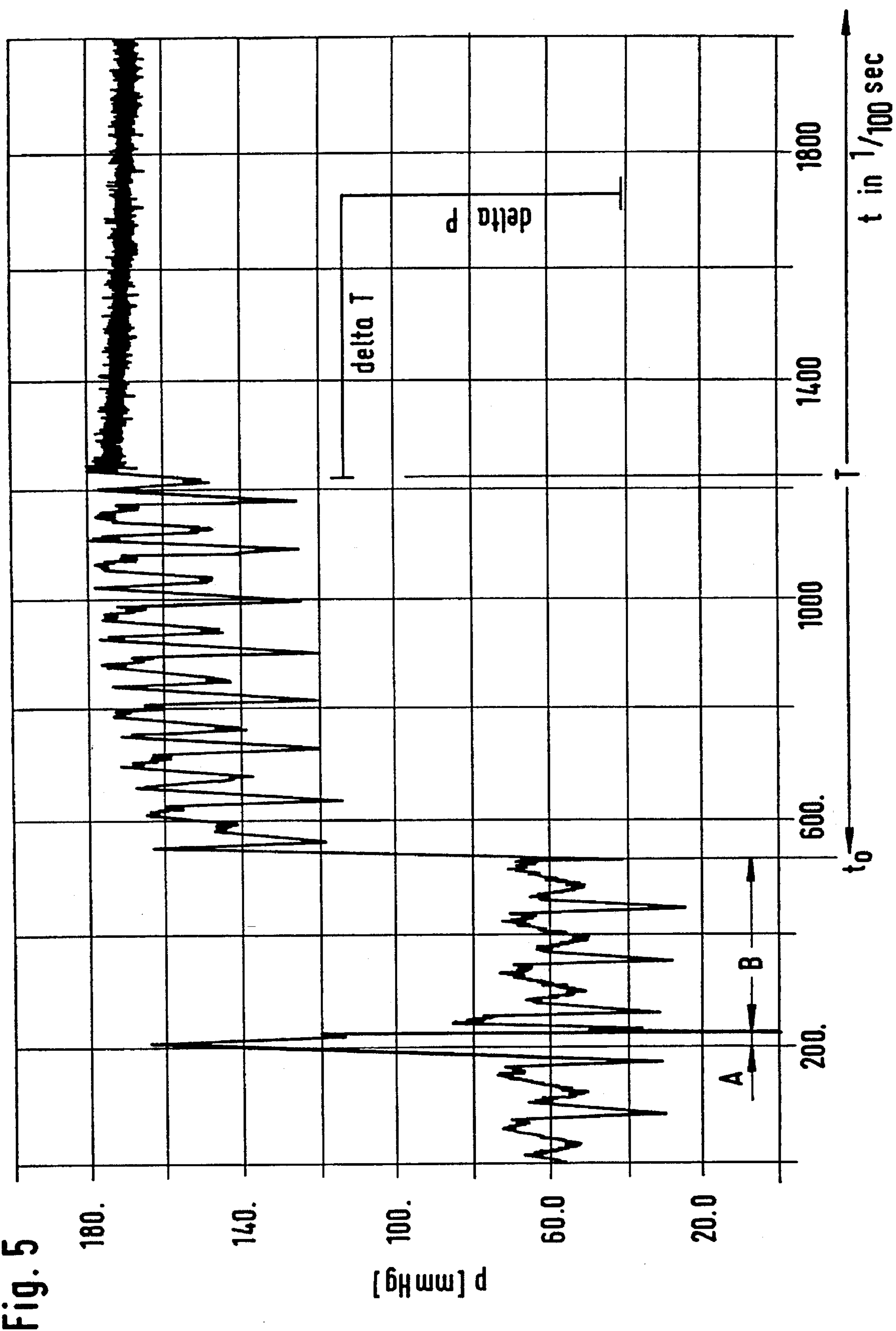
FIG. 5—the dialyzate pressure as a function of time in the pressure maintaining test according to the invention with an intact ultrafiltration control arrangement.
Figure 6:
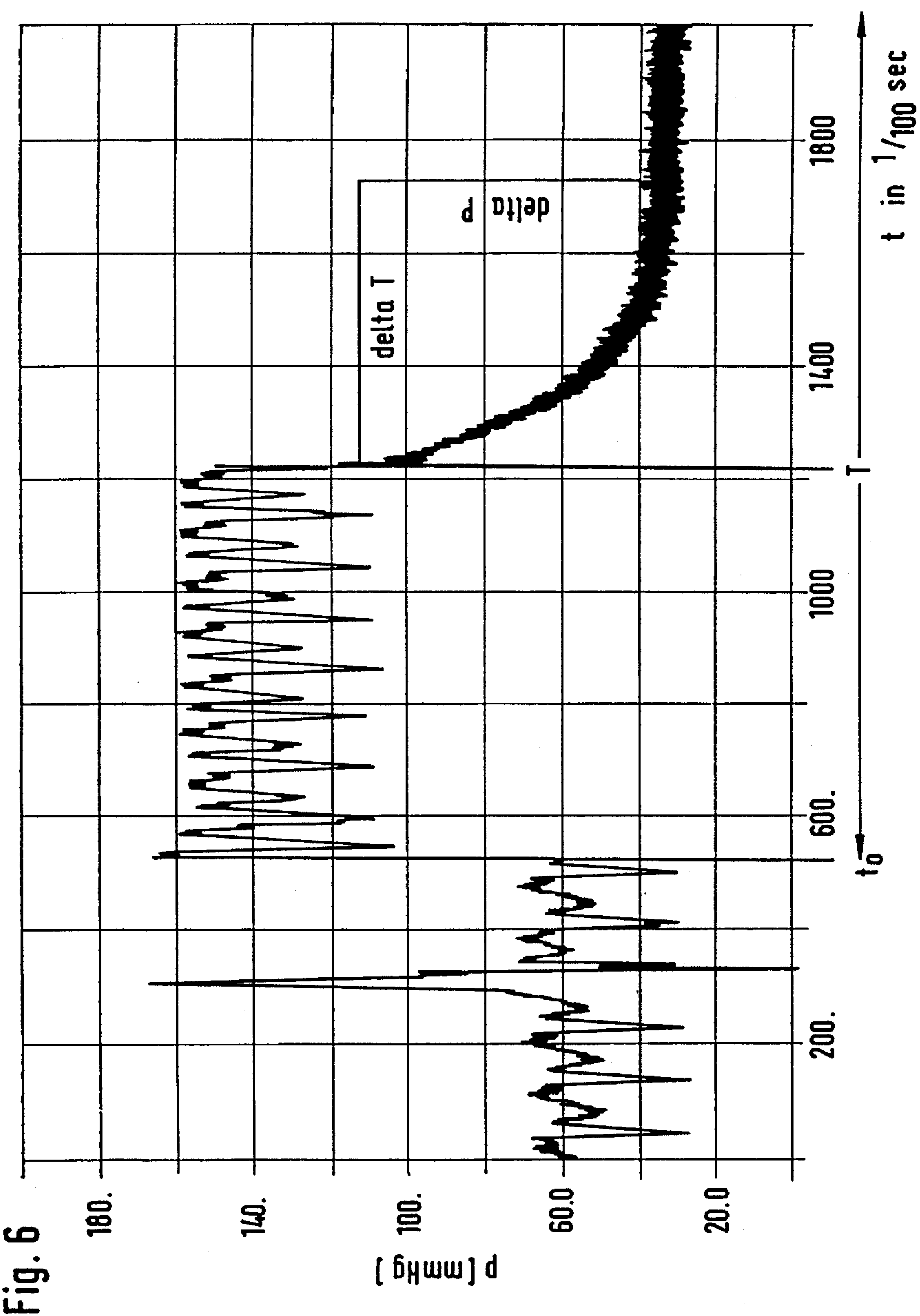
FIG. 6—the corresponding pressure as a function of time according to FIG. 5, but with a leak in the system.

The process according to the invention shall now be explained by reference to the curve courses (diagram) according to FIGS. 5 and 6. These figures respectively show the temporary march of the dialyzate pressure p(mmHg), on the basis of a test period of T-15 sec. FIG. 5 shows the march of pressure in the tight control system, and FIG. 6 shows the corresponding march of pressure in the case of a leak of 2.7 ml/min.

The left portion of the figures respectively shows the march of pressure on the basis of the operation of the balancing chambers 14 for two operating cycles A and B. The pressure peaks result from the switching of the operating cycles. This portion of the curve shall be described below by reference to FIGS. 3 and 4. During $t_o$ the dialyzer 1 is separated from the dialyzing liquid circuit for the duration of the test interval T, in that the dialyzer valves are closed and the bypass valve 17 is opened. The pressure respectively first rises, then balances out and remains stable if the system is tight (FIG. 5). In the case of a leak, on the other hand, it falls. This pressure decrease, as shown clearly in FIG. 6, is an unambiguous sign that the UF control system is no longer tight.

During the pressure holding test the dialyzer is switched off, but for a predetermined period of time the situation regarding operating pressure is nonetheless sufficiently realistic. The pressure holding test should typically be conducted within a time interval of 20 sec. max.

Since an error may occur at any point in time during treatment, the test must be performed periodically. This period depends on the UFC of the dialyzer. In a development of the invention it is therefore useful to make the interval between two pressure holding tests dependent on the UFC of the dialyzer. In the case of high UFC the limit of 0.5 l typically set for ultrafiltration error is already reached quickly, whereas in the case of a low UFC the period may be equal to the treatment period, i.e. the pressure holding test must not be performed at all, since the safety system already responds on the basis of the monitoring of the membrane pressure.

The duration of the period can be determined as follows: assuming a threshold value of 0.5 l for the ultrafiltration error and a resolution of the transmembrane pressure monitor of 20 mmHg, the monitor switches the hemodialysis apparatus to safe condition in the case of a deviation of more than 20 mmHg from the nominal value.

The UF quantity (ml) is equal to the product of ultrafiltration rate UFR (ml/h) and time t (min):

$$UF=UFR*t/60 \quad (1)$$

The ultrafiltration rate UFR is equal to the product of the ultrafiltration coefficient UFC (ml/h.mmHg) and pressure p (mmHg).

$$UFR=UFC*p \quad (2)$$

By inserting (2) in (1) the following result is obtained for the UF quantity:

$$UF=UFC*p*t/60 \quad (2a)$$

The period Δt can be calculated for the maximum error ΔUF on the basis of the UFC.

By solving the equation (2a) for Δt, the following result is obtained:

$$\Delta t=(\Delta UF/p)*(60/UFC) \quad (3)$$

For a UFC of 60 and a maximum UF error of 500 ml and a p of 20 mmHg, a period Δt of 25 min is obtained by introducing these values in equation (3).

From equation (3) it can be easily determined, by solving this equation for UFC, from which UFC onwards no test is any longer necessary. For this purpose the dialysis treatment period is introduced in the equation for Δt.

By introducing the value in the equation:

$$UFC=(\Delta UF/p)*(60/\Delta t)$$

A UFC of approximately 6 is obtained for a treatment period of 4 h.

When using dialyzers with a UFC larger than 6, the process according to the invention will therefore be performed in periodic intervals adapted to the respective UFC.

The process according to the invention can be performed manually. In the time intervals predetermined by the respective UFC of the dialyzer used, an operator respectively performs the switching operations to bypass the dialyzer and visually observes the march of pressure by monitoring the display of the pressure signal of the pressure transducer 22. If a leak is detected, the dialyzer is switched to safe state. If not, it is switched on again. In this manual test a modification of the dialysis apparatus is not necessary, i.e. the process can be performed with the existing apparatus.

Figure 2:
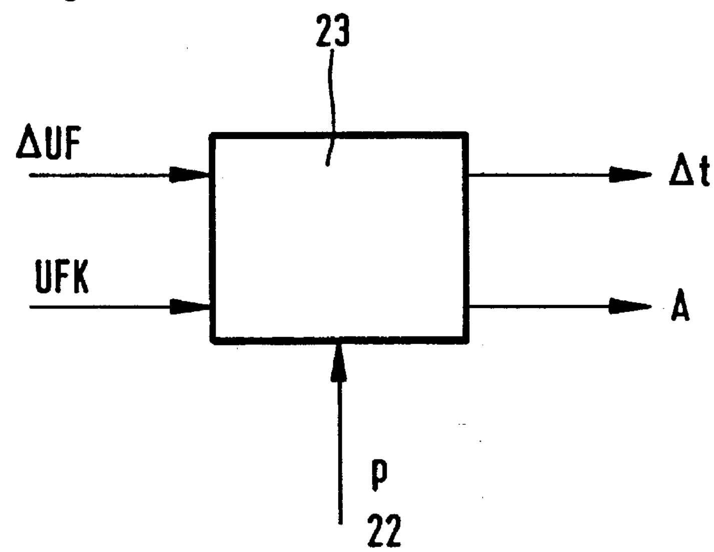
FIG. 2—an exemplary embodiment of the apparatus according to the invention presented in the form of a block diagram.

The above-specified steps can principally also be performed automatically, e.g. by using a microprocessor system 23 according to FIG. 2.

This microprocessor system calculates the necessary test period Δt with the assistance of equation (3) on the basis of recording the apparatus-specific values ΔUF, UFC and transmembrane pressure and initiates the necessary switching operations, displays and alarm signals via outlet A on the basis of the course of the (digitalized) pressure signal.

The described process according to the invention thus permits periodic detection of all defects in the ultrafiltration system which causes an ultrafiltration error above the specified threshold value.

The extraction of the ultrafiltrate from the dialyzing liquid circuit 1, as described above, is closely interrelated with the functioning method of the balancing chamber 14.

Although it is assumed in safety technology for medical apparatus that, in the treatment interval, only a single error will occur in a component arrangement (e.g. UF control arrangement), a process for detecting a defect in the balancing chamber system 14 without interrupting the dialysis would increase safety.

As explained above, the balancing chamber 14 consists of two like component systems, which are operated alternately with a predetermined operating cycle so as to obtain an equal flow. Very high standards must be required of the precision of the balancing arrangement. If a defect occurs in one of the systems, the balancing is disrupted during the operating cycle of the system concerned. This results in a small deviation of the dialyzing liquid pressure. This small deviation can, however, not be detected, since the pressure is influenced by fluctuations caused by the effect of the blood pump 4 and the UF pump 21, but also by the switching operation itself. To render this small deviation detectable, the pressure is determined and recorded for one cycle period respectively. The values thus collected for one balancing chamber system are then averaged and the variance is determined. As soon as the variance has fallen to the extent that a comparison is possible with the required resolution, the averaged values of the two chambers are compared and, in the case of a deviation higher than a predetermined amount (typically 4 mmHg for a UFC of the dialyzer of 40) an alarm signal is emitted. This threshold value can now be made dependent on the UFC of the dialyzer. In the case of a low UFC, the same leak rate, of course, results in a higher pressure differential.

Figure 3:
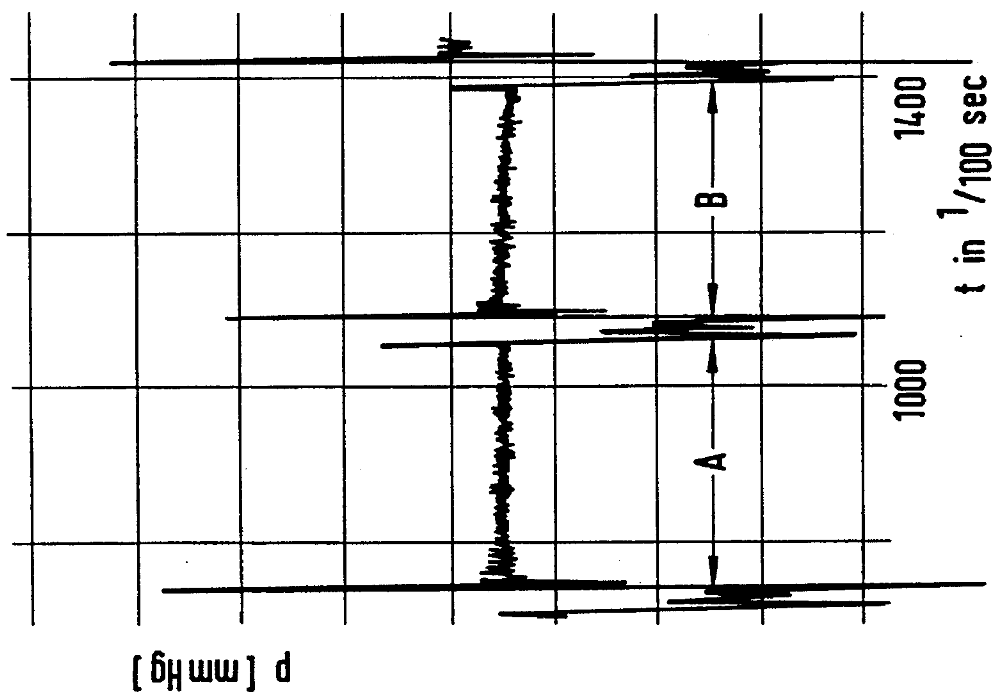
FIG. 3—the dialyzate pressure as a function of time on the intact balancing system of the hemodialysis apparatus according to FIG. 1.

FIG. 3 shows the temporary march of the dialyzate pressure p in the mmHg in a tight balancing system for two balancing chamber intervals A and B. The pressure peaks result from the switching of the balancing chambers. It can be recognized that the pressure is flat in both intervals.

Figure 4:
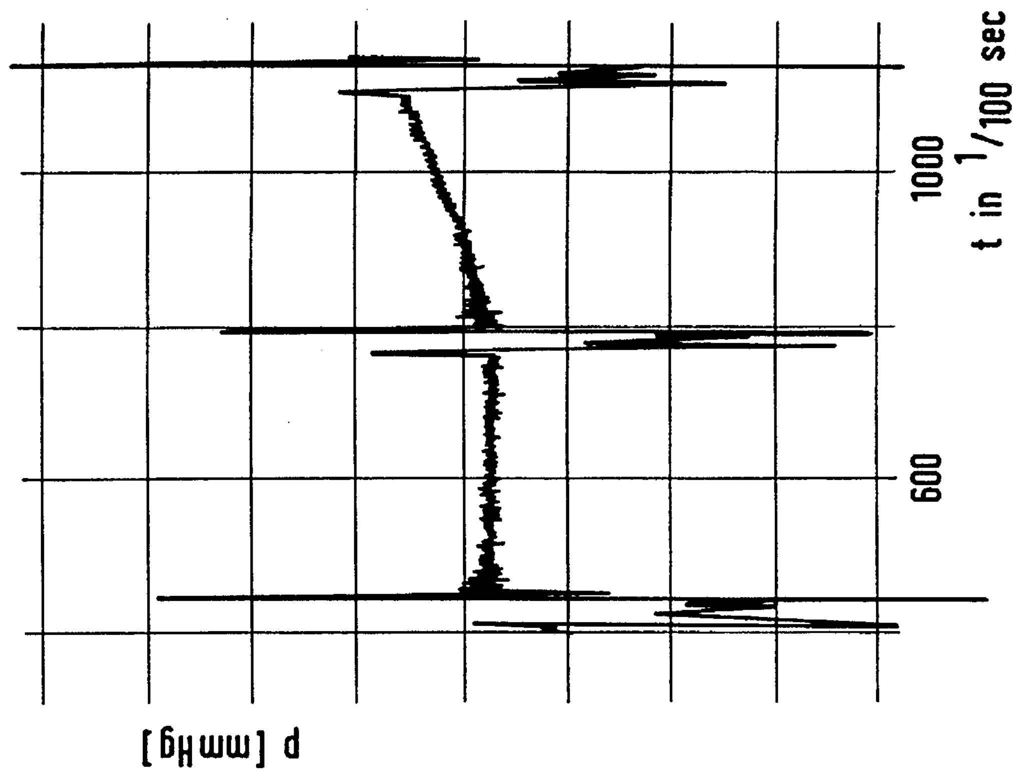
FIG. 4—the same diagram as in FIG. 3, but with a defect in the balancing system.

FIG. 4 shows the march of pressure as in FIG. 3, but one balancing chamber has a leak resulting in an ultrafiltration error of approximately 2 ml/min. It is recognizable that the march of pressure is rising in one part and flat in the other. As described above, this readily permits detection of the presence of a leak.

A range of devices, in particular of an electronic and digital nature, are available to the person skilled in the art for the circuit organization of the above-specified processes.

Figure 7:
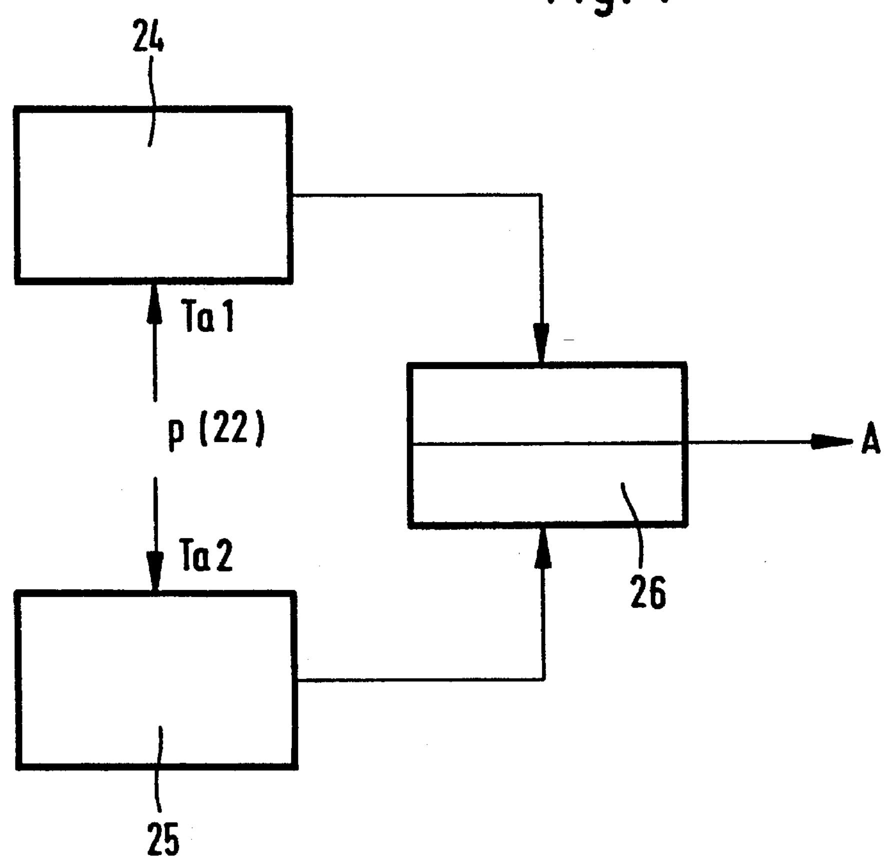
FIG. 7—a block diagram of a control for determining a defect in the balancing system of the hemodialysis apparatus according to FIG. 1.

FIG. 7 shows a corresponding circuit arrangement for one of the balancing chambers 14 in schematic presentation. A corresponding circuit arrangement is to be provided for the second balancing chamber. The circuit arrangement according to FIG. 7 comprises two units or stages 24 and 25, of which stage 24 is associated with the operating cycle 1, i.e. one of the chamber halves of the balancing chamber, and stage 25 is associated with operating cycle 2, i.e. the other chamber half. These stages respectively record the suitably prepared pressure signal p from pressure transducer 22 which is averaged for the working cycle. Respective electronic switches for these stages for recording mean values are known to the person skilled in the art.

The values pertaining respectively to one chamber section are recorded and averaged in the subsequent stage 26, whereby the mean values in the stage are compared with each other. As soon as the deviation exceeds a value predetermined in stage 26, an alarm signal is generated at the outlet A and, if appropriate, a switching operation is initiated. If suitable, a display is also simultaneously effected. For stage 26, respective circuit arrangements for recording, averaging and comparing signals are also available to the person skilled in the art, in particular digital ones. All stages can, moreover, be simulated by a microprocessor.

I claim:

1. A method for monitoring the operability of components in a hemodialysis apparatus which comprises a dialyzer and a dialyzing liquid circuit, comprising:

isolating said dialyzer from said dialyzing liquid circuit for a predetermined time interval T during dialysis treatment so that dialyzing liquid within said dialyzing liquid circuit bypasses said dialyzer, said dialyzing liquid having a mean dialyzate operating pressure;

measuring pressure in said dialyzing liquid circuit during said time interval T; and monitoring said pressure to detect a deviation from said mean dialyzate operating pressure while continuing to allow said pressure to freely fluctuate.

2. The method of claim 1, wherein said time interval T is approximately 20 seconds.

3. The method of claim 1, wherein said isolating step is performed by closing an isolation valve and opening a bypass valve so that dialyzing liquid flows through a bypass line.

4. The method of claim 1, wherein said isolating step is repeated after a time period Δt, wherein Δt is defined as $$\Delta t=(\Delta UF/P*(60/UFC)),$$

wherein ΔUF is the maximum ultrafiltration error of said dialyzer, P is the transmembrane pressure of said dialyzer, and UFC is the ultrafiltration coefficient (ml/h-mmHg) of said dialyzer.

5. The method of claim 1, further comprising:

displaying said measured pressure for visual observation.

6. The method of claim 1, further comprising:

switching said dialyzer into said dialyzing liquid circuit after said monitoring step if said deviation is not detected.

7. The method of claim 6, wherein said switching step is performed by opening an isolation valve and closing a bypass valve so that dialyzing liquid flows through said dialyzer.

8. The method of claim 1, further comprising:

switching said dialyzer to a safe state after said monitoring step if said deviation is detected.

9. The method of claim 1, wherein said isolating, measuring, and monitoring steps are performed automatically by said hemodialysis apparatus.

10. The method of claim 1, wherein said measuring step is performed using a pressure transducer.

11. An apparatus for monitoring the operability of components in a hemodialysis apparatus which comprises a system having a dialyzer and a dialyzing liquid circuit, comprising:

means for isolating said dialyzer from said dialyzing circuit for a predetermined time interval T during dialysis treatment so that dialyzing liquid within said dialyzing liquid circuit bypasses said dialyzer, said dialyzing liquid having a mean dialyzate operating pressure;

a pressure transducer operable for measuring pressure in said dialyzing liquid circuit during said time interval T;

means for monitoring said measured pressure to detect a deviation from said mean dialyzate operating pressure;

control means for actuating said means for isolating, and for controlling operation of said pressure transducer and said means for monitoring at a selected time during dialysis treatment; and means responsive to said detecting to change the operating state of the system.

12. The apparatus of claim 11, wherein said control means comprises a microprocessor.

13. The apparatus of claim 11, further comprising:

means for displaying said measured pressure.

14. The apparatus of claim 11, further comprising:

means for switching said dialyzer into said dialyzing liquid circuit.

15. The apparatus of claim 14, wherein said means for switching comprises an isolation valve and a bypass valve.

16. A method for monitoring the operability of a component in a hemodialysis apparatus which comprises a chamber in a dialyzing liquid circuit having first and second chamber sections, said first chamber section receiving dialyzing liquid during first working cycles of said chamber and said second chamber section receiving dialyzing liquid during second working cycles of said chamber, said method comprising:

measuring and averaging the pressure in said first chamber section during one of said first working cycles to obtain an average individual working cycle pressure for said first chamber section;

measuring and averaging the pressure in said second chamber section during one of said second working cycles obtain an average individual working cycle pressure for said second chamber section;

obtaining a plurality of said average individual working cycle pressures for said first chamber section and averaging said plurality of said average individual working cycle pressures for said first chamber section to obtain an average composite working cycle pressure for said first chamber section;

obtaining a plurality of said average individual working cycle pressures for said second chamber section and averaging said plurality of said average individual working cycle pressures for said second chamber section to obtain an average composite working cycle pressure for said second chamber section;

comparing said average composite working cycle pressure for said first chamber section and said average composite working cycle pressure for said second chamber section to obtain a difference value; and generating an alarm if said difference value exceeds a threshold value.

17. The method of claim 16, further comprising:

determining said threshold value based upon an ultrafiltration coefficient of said dialyzer.

18. An apparatus for monitoring the operability of a component in a hemodialysis apparatus which comprises a chamber in a dialyzing liquid circuit having first and second chamber sections, said first chamber section receiving dialyzing liquid during first working cycles of said chamber and said second chamber section receiving dialyzing liquid during second working cycles of said chamber, said apparatus comprising:

means for measuring the pressure in said first chamber section during one of said first working cycles to thereby produce a first pressure signal;

means for measuring the pressure in said second chamber section during one of said second working cycles to thereby produce a second pressure signal; and electronic control means, wherein said electronic control means comprises, first input means for receiving said first pressure signal and for generating an average individual first pressure signal for said one first working cycle, second input means for receiving said second pressure signal and for generating an average individual second pressure signal for said one second working cycle, averaging means for averaging said average individual first pressure signals for a plurality of said first working cycles to generate an average first pressure signal, and for averaging said average individual second pressure signals for a plurality of said second working cycles to generate an average second pressure signal, comparing means for comparing said average composite first pressure signal and said average composite second pressure signal to generate a difference value, and generating means for generating an alarm signal if said difference value exceeds a threshold value.

19. Apparatus according to claim 18, wherein said electronic control means comprises a microprocessor.

20. Apparatus according to claim 18, wherein said means for measuring the pressure in said first chamber section comprises a pressure transducer.

21. Apparatus according to claim 18, wherein said means for measuring the pressure in said second chamber section comprises a pressure transducer.

* * * * *